(12) United States Patent  
Gong

(10) Patent No.: US 7,985,442 B2  
(45) Date of Patent: Jul. 26, 2011

(54) PATTERNED MOLD FOR MEDICAL DEVICE

(75) Inventor: Victoria M. Gong, Sunnyvale, CA (US)

(73) Assignee: Abbott Laboratories Corporation, Abbott Park, IL (US)

( * ) Notice: Subject to any disclaimer, the term of this patent is extended or adjusted under 35 U.S.C. 154(b) by 0 days.

(21) Appl. No.: 12/917,194

(22) Filed: Nov. 1, 2010

(65) Prior Publication Data

US 2011/0045164 A1 Feb. 24, 2011

Related U.S. Application Data

(62) Division of application No. 11/939,275, filed on Nov. 13, 2007, now Pat. No. 7,832,251.

(60) Provisional application No. 60/865,995, filed on Nov. 15, 2006.

(51) Int. Cl.  
*A61F 2/06* (2006.01)  
*A61L 33/00* (2006.01)  
*B05D 5/00* (2006.01)

(52) U.S. Cl. ....... 427/2.1; 427/256; 623/1.15; 623/1.38; 623/901; 72/414; 29/283.5

(58) Field of Classification Search ................... 427/2.1, 427/256; 623/1.15, 1.2, 1.21, 1.22, 1.18, 623/1.38, 901; 72/414, 416; 29/283.5, 515  
See application file for complete search history.

(56) References Cited

U.S. PATENT DOCUMENTS

| | | | |
|---|---|---|---|
| 6,190,404 B1 * | 2/2001 | Palmaz et al. | 623/1.15 |
| 7,832,251 B2 * | 11/2010 | Gong | 72/414 |
| 2002/0050220 A1 * | 5/2002 | Schueller et al. | 101/486 |
| 2006/0229711 A1 * | 10/2006 | Yan et al. | 623/1.38 |
| 2007/0110888 A1 * | 5/2007 | Radhakrishnan et al. | 427/2.1 |

* cited by examiner

Primary Examiner — David B Jones  
(74) Attorney, Agent, or Firm — Baker Botts L.L.P.

(57) ABSTRACT

An apparatus and method for imprinting a pattern on a medical device to provide a surface with greater surface area and improved adhesion properties.

25 Claims, 3 Drawing Sheets

PATTERNED MOLD FOR MEDICAL DEVICE

CROSS REFERENCE TO RELATED APPLICATIONS

This application is a divisional application of U.S. application Ser. No. 11/939,275, filed Nov. 13, 2007, now U.S. Pat. No. 7,832,251, which claims the benefit of U.S. Provisional Patent Application Ser. No. 60/865,995, filed Nov. 15, 2006, the disclosure of each of which is incorporated herein by reference in its entirety.

TECHNICAL FIELD OF THE INVENTION

The present invention relates generally to an apparatus for imprinting a pattern on a surface of a medical device. More particularly, the invention relates to a mold for defining cavities or protrusions on a surface of a medical device such as a stent or catheter. The invention also relates to a method of imprinting a pattern onto the medical device.

BACKGROUND OF THE INVENTION

Stents are generally tubular shaped implantable devices that are expand radially to hold open a segment of a blood vessel after implantation into an anatomical lumen. Stents are generally introduced into the anatomical lumen by a stent delivery device, such as a catheter assembly. It has been found that polymer coated stents are advantageous in providing the intravascular stent with a smooth surface and can be utilized to serve as a vehicle or carrier of therapeutic agent. In this regard, the coated stents often contain multiple layers of polymer material applied to the surface of the stent.

A well-known method for manufacturing a coated stent involves applying a polymer coating onto the desired surface of the stent by dipping or spraying techniques, for example, or other known techniques.

In addition to multilayered stents, other medical devices such as stent delivery devices also include components that can be coated or multilayered. For example, U.S. Pat. No. 6,663,614 to Carter, which is incorporated herein in its entirety, discloses a catheter shaft having at least two polymeric layers to provide better pushability and/or a variable flexibility along the length of the catheter shaft. As yet another example, U.S. Pat. No. 7,025,752 to Rice, the entire content of which is incorporated herein, discloses a balloon having multiple coatings of lubricious material. Accordingly, many different types of multilayered medical devices are currently utilized in medical applications.

One drawback in the process of manufacturing multilayered medical devices, such as coated stents or multilayered catheter shafts is poor adhesion of the multiple polymeric coatings to each other or to the surface of the medical device. For example, and as described in U.S. Pat. No. 6,805,898 to Wu, which is incorporated herein in its entirety, discloses that a poorly adhered coating on a stent can be rubbed and peeled off of the stent if the coating contacts an arterial wall while the stent is being moved into position. Wu further discloses that the problem of poorly adhered coating material can promote thrombosis and restenosis, by providing additional surfaces for platelets and other blood components to adhere and can lead the loss of a significant amount of the drugs to be delivered from the coating.

Wu attempts to solve the problem of poorly adhesion by providing a medical device such as a stent or graft with asperities on the outer surface to improve retention of one or more layers of coatings on the device. According to Wu, the asperities are formed on the surface of the medical device by the removal of material by chemical etching techniques.

Thus, there remains a need for efficient and economic systems and methods for manufacturing a coated or multilayered medical device, which will also improve adhesion properties of the coating or multiple layers to the medical device.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied herein and broadly described, the invention includes an apparatus for imprinting a pattern on a surface of a medical device. The apparatus comprises an outer body configured and dimensioned to facilitate the application of an imprint on a surface of a medical device and an inner body having a generally tubular shape, an outer surface, an inner surface, and a lumen therebetween. The inner body is disposed in the lumen of the outer body and includes a pattern along at least a portion of the inner surface. In operation, a medical device is positioned in the lumen of the inner body and the outer body is compressed so that the pattern along the surface of the inner body is imprinted on the surface of the medical device. In this regard, the medical device can be a stent, graft, catheter shaft or a balloon.

The outer body and the inner body may be a unitary construction or separate components. For example and not limitation, the outer body can be a crimping tool and the inner body can be a mold.

Advantageously, the inner body may be interchangeable with at least one other inner body having an inner surface including a pattern along a length thereof. In this regard, patterns of the interchangeable inner bodies can be different. For example and not limitation, the pattern along the surface of the inner body can include a variety of shapes. For example, it can include at least one projection, at least one cavity, or a combination thereof. Furthermore, the at least one projection may have a height extending outwardly from the inner surface of the inner body. The at least one cavity may have a depth extending inwardly from the inner surface of the inner body. According to another aspect of the invention, the imprint surface may include a plurality of projections extending outwardly from the imprint surface, a plurality of cavities extending inwardly from the imprint surface, or a combination thereof. The projections may further include a height and a diameter. The cavities may include a depth and a width. The plurality of projections may include at least some projections having a varied diameter, a varied height, or varied diameter and height. Likewise, the plurality of cavities may include at least some cavities having a varied depth, a varied width, or a varied depth and width. Alternatively, the at least one of the projections or at least one of the cavities may have a polygonal or linear shape. The plurality of projections or plurality of cavities may include a circular, square or linear shape.

The at least one projection may include a plurality of projections and the at least one cavity can include a plurality of cavities. The plurality of projections can include two or more projections having a varied height. The plurality of cavities can include two or more cavities having a varied depth. Alternatively, the at least one projection or cavity can have a polygonal or linear shape.

In another aspect of the invention, mold is provided for imprinting a pattern on a surface of a medical device, the mold includes a generally tubular body having an inner surface, an outer surface and a lumen therebetween. The inner surface includes an imprint surface along a portion thereof and the lumen is configured to receive a medical device. The inner surface is configured to transfer a pattern to a surface of the medical device in the lumen mold. In operation, the mold is compressed to transfer the imprint on the surface of the medical device received in the lumen of the mold. In this manner, an outer body is not required.

In accordance with another aspect of the invention, a method is provided for imprinting a pattern onto a surface of a medical device. The method includes providing a medical device having a surface; imprinting a pattern on the surface of the medical device; and applying a coating material to the patterned surface of the medical device.

The method may also include placing a mandrel in the lumen of the tubular structure and imprinting the pattern on an outer surface of the medical device. The medical device may be a stent, graft, shaft or balloon. The patterned surface may be at least a portion of the surface of the medical device.

The layer of coating may be applied to the surface of the medical device by at least one of spraying, jetting, dipping techniques, or various other standard coating techniques. The coating material may include at least one polymer or at least one therapeutic agent. The at least one polymer may be phosphorylcholine. The at least one therapeutic agent may be rapamycin.

In accordance with the method, the imprinting step may further include imprinting a pattern on a coated surface of the medical device. The coated surface of the medical device may include at least one therapeutic agent. The coating material applied to the patterned surface of the medical device may be configured to control the release of the at least one therapeutic agent.

The applying step may include applying a second coating to at least a portion of the patterned surface of the medical device.

DESCRIPTION OF THE DRAWINGS

For a more complete understanding of the present invention, and the advantages thereof, reference may be made to the following description of exemplary embodiments, taken in conjunction with the accompanying drawings, in which.

DETAILED DESCRIPTION OF THE PREFERRED EMBODIMENTS

Figure 1:
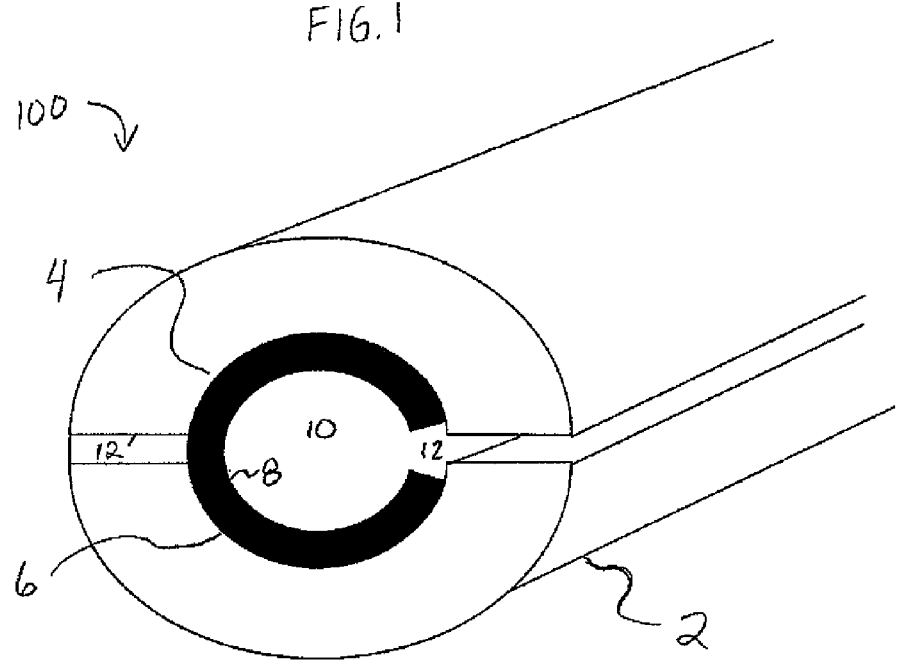
FIG. 1 is a schematic representation of one embodiment of the present invention.

Reference will now be made in detail to the present preferred embodiments of the invention, an example of which is illustrated in the accompanying drawing. The method and corresponding steps of the invention will be described in conjunction with the detailed description of the apparatus.

The methods and apparatus presented herein may be used for imprinting a pattern onto the surface of a medical device. The present invention is particularly suited for manufacturing a medical device having multiple polymer coatings. For purpose of explanation and illustration, and not limitation, an exemplary embodiment of the apparatus in accordance with the invention is showed in FIG. 1 and is designated generally by reference character 100.

In accordance with the invention, and as depicted in FIG. 1, the apparatus 100 generally includes an outer body 2 and an inner body 4. The inner body includes an inner surface 8 having a pattern along at least a section thereon (not shown). In one embodiment, each of the inner and outer bodies of the invention include a generally C-shaped member. Each generally C-shaped member has a proximal end distanced from a distal end to define a spacing therebetween 12 and 12'. Accordingly, the outer body 2 is configured and dimensioned to compress the inner body to facilitate the transfer of an imprint corresponding the pattern on the inner surface of the inner body to the surface of a medical device, which is disposed in the lumen of the inner body. In this regard, the outer body can be a crimping device which assists in crimping the pattern onto the surface of the medical device. The medical device, can be for example but not limitation, a stent or graft. Alternatively, the medical device can be a tubular member such as a catheter shaft or balloon.

The outer body 2, as depicted in FIG. 1 can be a tubular member having a proximal end and distal end and a lumen therebetween. However, alternative dimensions of the outer body can be utilized, if desired. For example, the outer body can be a cylindrical member and not a tubular member.

Figure 2:
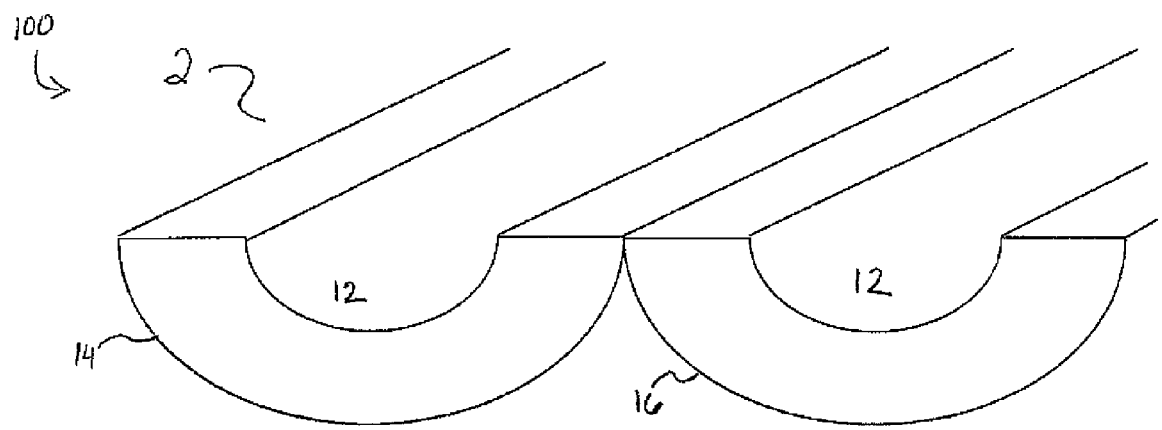
FIG. 2 is a schematic representation of the outer body of the present invention.

In one embodiment, as depicted in FIG. 2, the outer body can be constructed to comprise a first portion 14 pivotably engaged to a second portion 16. For example, a hinge joint can be disposed between the first and second portions. Alternatively, the outer body can be a unitary construction, if desired.

As would be appreciated by one skilled in the art, the dimensions of the outer body are dependent upon the application. For example, if the apparatus is utilized for imprinting a pattern on a stent, the outer body may optimally be constructed to have any desired length. In one preferred embodiment, the length is about 8 mm to about 80 mm, depending on whether the stent is a coronary or peripheral stent. In contrast, if the apparatus is utilized for imprinting a pattern on a catheter shaft, the outer body may optimally be constructed to have a length of about 100 cm to about 150 cm. Alternatively, the outer body can be constructed to have any desired length suitable for the intended application.

A variety of materials can be utilized to form the outer construction. For example, the outer body can be formed of metal, metal alloy, or polymer. The outer body can be formed from various grades of stainless steel, surgical steel or any non-shedding, non-reactive metals. Additionally, suitable tempered plastics may also be used. For example and not limitation, the suitable tempered plastics preferably exhibit sufficient hardness to facilitate transfer of an imprint to a device having sufficient malleability.

The inner body 4 is disposed in the lumen of the outer body such that the outer surface 6 of the inner body is at least partially in contact with the inner surface 14 of the outer body, as depicted in FIG. 1. In one embodiment, the inner body has a tubular body including a proximal end, a distal end and a lumen 10 therebetween to receive the medical device to be imprinted. The inner body can be formed from a variety of materials including grades of stainless steel, surgical steel, high-density polypropylene, polyether ether ketone (PEEK), teflon, etc. Dimensions could encompass surface areas extending from about 8 mm×8 mm to about 150 cm×150 cm.

In operation, a compressive force applied to the outer body facilitates the transference of the pattern disposed on the inner surface of the inner body in the form of an imprint to the medical device received in the lumen of the inner body. The during of the impression is dependent upon the malleable characteristics of the surface of the medical device. If desired, a lubricant, such as but not limited to styrenated phenol, can be applied to the inner surface of the inner body to prevent the inner body from adhering to the surface of the medical device.

The inner body can have a variety of patterns along a length thereof The pattern can be disposed along the entirety of the inner surface of the inner body or alternatively the pattern can be disposed along only a portion of the inner surface of the inner body. Generally, the pattern can include at least one projection, at least one cavity, or a combination thereof In this regard, the at least one projection has a height extending from the surface of the inner body and the at least one cavity has a depth extending in the surface of the inner body. Accordingly, the at least one projection will form a cavity in the surface of the medical device and the at least one cavity will form a projection in the surface of the medical device. The at least one cavity and the at least one projection can include a plurality of cavities and projections.

Where a plurality of projections are included to form the pattern, the plurality of projections can include projections having varied height. In this manner, the surface of the medical device will have corresponding depressions of varied depths in the imprinted surface. Likewise, where a plurality of cavities are included in the pattern along the inner body, the plurality of cavities can include cavities of varied depth.

Figure 3:
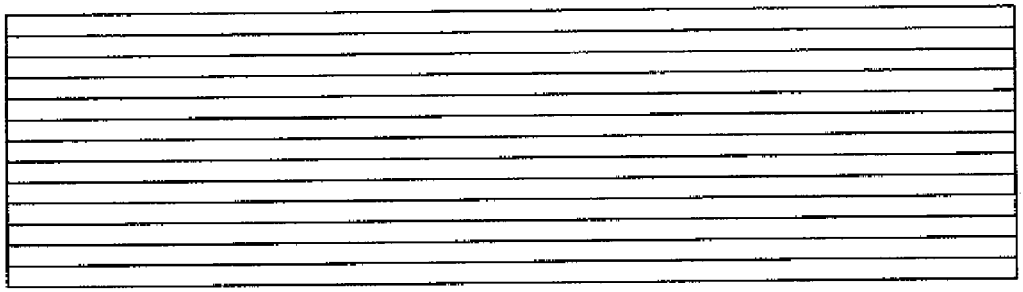
FIG. 3 is a schematic representation of the pattern of the present invention.
Figure 4:
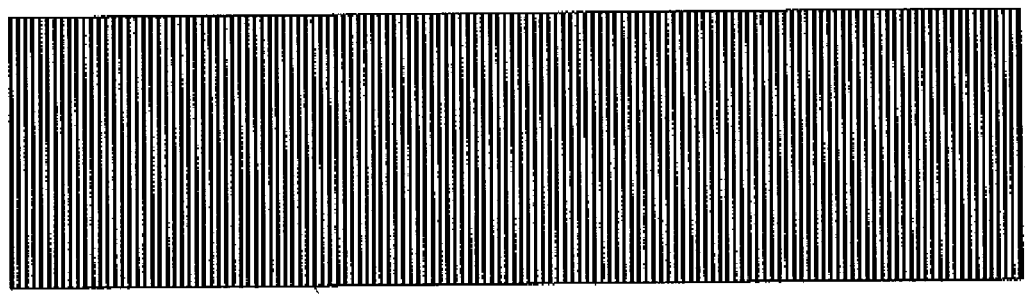
FIG. 4 is a schematic representation of a second embodiment of the pattern of the present invention.

The projections and cavities that form the pattern can include a number of shapes, several examples of which are depicted in FIGS. 3-8. For the purpose of illustration and not limitation, as depicted in FIG. 3, the at least one projection 20 or cavity 22 can include a longitudinal, linear dimension. In this manner, the linear pattern can extend across a vertical plane of the surface of the inner body, as shown in FIG. 3. Alternatively, the at least one projection or cavity can include longitudinal or linear dimension across a horizontal plane of the surface of the inner body, as depicted in FIG. 4.

Figure 5:
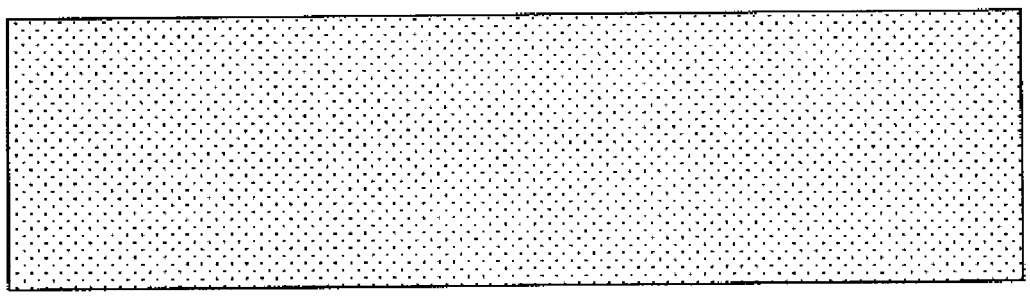
FIG. 5 is a schematic representation of a third embodiment of the pattern of the present invention.
Figure 8:
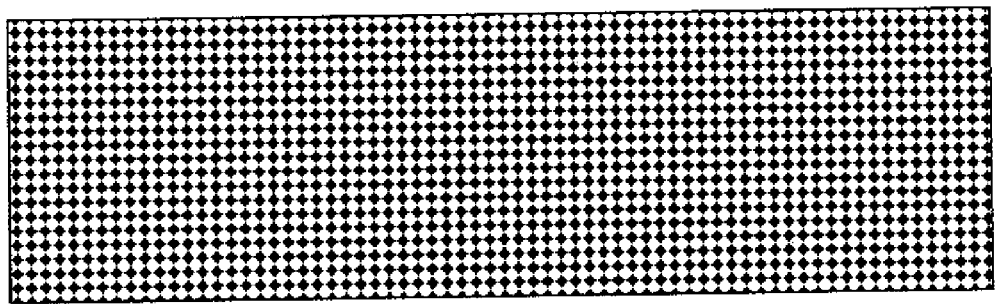
FIG. 8 is a schematic representation of a sixth embodiment of the pattern of the present invention.

In addition to or in lieu of the projections or cavities having a linear dimension, the at least one projection or cavity can include members having a circular dimension, as depicted in FIG. 5. The circular member has a predetermined diameter. If desired, at least some of the projections or cavities can include members having a varied diameter. The size of the diameter can be relatively small such that in the case of a projection, the projection member defines a pin shaped member, as depicted in FIG. 5. Alternatively, as depicted in FIG. 8, the at least one projection or cavity can have a larger diameter. As shown and depicted in FIG. 8, the projection member having a larger diameter can define a rod shaped member. Further, the diameters of each of the projections or cavities of a plurality can be constant, as depicted in FIGS. 5 and 8. Alternatively, if desired, some of the projections or cavities of the plurality can include a smaller diameter than other projections of the plurality to define a pattern including plurality of projections or cavities having a varied diameter. Further, the plurality of projections can include two or more projections having a varied height and the plurality of cavities can include two or more cavities having a varied depth. In this regard, the term "height" refers to the length of the projection extending outwardly from the inner surface of the inner body and the term "depth" refers to the length of the cavity extending inwardly from the inner surface of the inner body.

For example and not limitation, the height of at least one projection can be from about 1 to about 10 microns in thickness for a stent, depending on the thickness of the coating. Typical stent coating thicknesses of drug eluting stents range from 7 um to 20 um. The projection height may also extend to a few millimeters if the coating is thicker.

In accordance with an aspect of the invention, the projections and cavities formed in the surface of the medical device may have a height and depth, respectively, that is on the scale of from a few nanometers to 1 micron. Projections and cavities of such a size may be referred to as nano or micro scale projections or cavities. Nano or micro scale projections and cavities act as surface texturing of the medical device.

A textured surface on the medical device increases the surface area of the medical device, which upon placement into the body, increases the degree of tissue in-growth as between the wall of a body lumen and the medical device. Additionally, a textured surface on a medical device may increase the adhesion of a coating layer to the medical device surface. The dimensioning of the height and depth of the projections and cavities, respectively may be selected as suitable for a particular medical device, application, or coating material.

Figure 6:
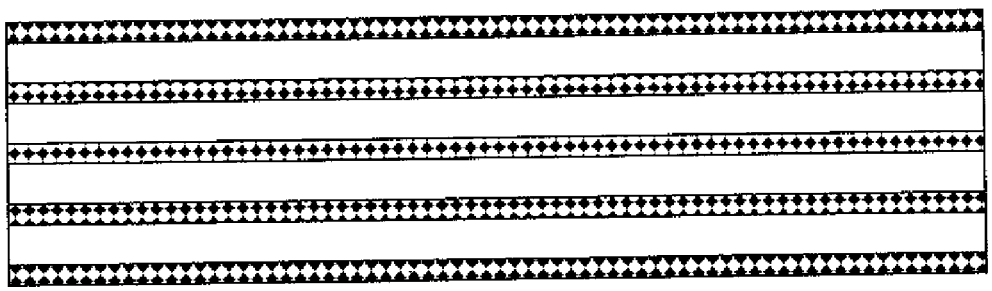
FIG. 6 is a schematic representation of a fourth embodiment of the pattern of the present invention.

As discussed above, the projections and cavities can include members having a variety of shapes and sizes. As depicted in FIG. 6, the pattern can include a plurality of projections having circular shaped members and a plurality of cavities having a different shaped members, such as a square shaped members.

Figure 7:
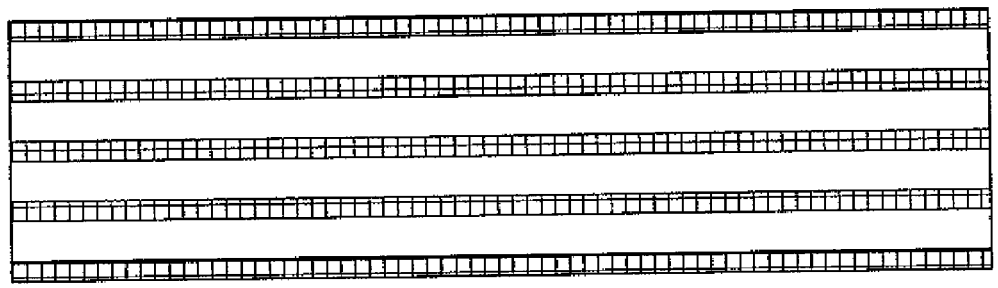
FIG. 7 is a schematic representation of a fifth embodiment of the pattern of the present invention.

As shown and depicted in FIG. 7, the at least one cavity can include a plurality of cavities regularly disposed along the longitudinal plane of the inner member. The plurality of cavities can include square shaped members regularly disposed along the longitudinal plane of the inner body. For stents, catheters, and other devices that are horizontally structured, a pattern having axial constructs is preferred. For devices having spherical, disc-shaped or ellipsoidal structures, a convex dimension is preferred.

As embodied herein and depicted in FIGS. 3 to 7, the inner body can be configured to include a multitude of patterns along a length thereof. In this manner, the invention can further include a plurality of interchangeable inner bodies having different patterns along a length of the interchangeable inner body. Accordingly, the apparatus has the advantage of being capable of imprinting different patterns depending on the pre-selected interchangeable inner body chosen by the user. In this regard, the plurality of inner bodies can be a plurality of molds, each mold having a different pattern along a surface thereof.

In one aspect of the invention, the medical device received in the lumen of the inner body can be a coated medical device, such as but not limited to a coated stent or coated catheter shaft. The imprint of the selected pattern to the coated surface of the stent or medical device provides a transference of at least one cavity or at least one projection to the surface of the stent or other medical device. The at least one projection or at least one cavity on the surface of the medical device provides the surface with a greater surface area. Accordingly, the at least one projection or at least one cavity allows two or more layers of coating to having improved adhesion qualities to each other and to the medical device. In this manner, an improved multilayered medical device can be manufactured without the need for removing material from the medical device as by chemical etching techniques, which can damage the qualities of the medical device, as disclosed in U.S. Pat. No. 6,805,898 to Wu. Accordingly, the present invention provides a more efficient and economic apparatus and method for making a multilayered medical device.

Further, the medical device is not required to be pre-coated to be within the spirit of this invention. In this manner, the present invention can be used to imprint the surface of a bare medical device, such as a bare or uncoated stent. In this regard, the bare stent comprises metal, metal alloy, or polymer material and is uncoated. In this manner, the imprint pattern on the surface of the bare stent provides a greater surface area for adhesion of a polymeric coating applied to the bare stent. For this aspect of the invention, the inner body should be composed of a harder grade material than the bare device.

In another aspect of the invention, a mold is provided for imprinting a pattern on a surface of a medical device. The mold includes a generally tubular body having an inner surface, an outer surface and a lumen therebetween. The inner surface of the mold includes a pattern along a portion thereof. In this manner, the mold is a crimping device that receives a medical device in the lumen. The mold is crimped to transfer an imprint of the pattern to the surface of the medical device. In this manner, the mold does not require an outer body, as described above.

Current stent delivery system manufacturers use crimp machines in which a set of 10-15 individual "teeth" (of normally triangular shape) are oriented in a circle. The teeth are spaced far apart (with the circle diameter at its maximum) and during the crimping operation, the individual teeth are uniformly brought closer together (with the circle diameter at its minimum). According to another aspect of the invention, the mold can be attached to the tips of the teeth. This configuration would require that the mold be placed precisely with respect to the teeth of the crimp machine.

In yet another aspect of the invention, a method is provided for imprinting a pattern on a surface of a medical device. The method comprises the steps of providing a medical device having a surface; imprinting a pattern on the surface of the medical device, and applying a coating material to the patterned surface of the medical device. For the purpose of illustration and not limitation, the medical device can be a stent, graft, catheter shaft, balloon or other medical device. The surface of the medical device can be bare or pre-coated, if desired. The pattern imprinted to the surface of the medical device preferably includes at least one projection or cavity to define a surface having a greater area for improved adhesion qualities.

In one embodiment, the medical device is a tubular member having a lumen therein. In this regard, a mandrel can be placed in the lumen of the tubular medical device so that the force applied to the medical device during the imprint step does force the medical device to collapse. In this manner, the mandrel assists in maintaining the lumen of the medical device. As discussed above, the medical device can be a stent, graft, catheter shaft or balloon. However, it should be recognized that a wide variety of other medical devices can be used. As discussed above, the imprint of the at least one projection 20 and/or the at least one cavity 22 provides the surface of the medical device with a greater surface area and thus promotes adhesion of a coating to the medical device. Preferably, the imprinted pattern includes a plurality of projections and/or cavities along at least a portion of the surface of the medical device.

The method of the invention, for example and not limitation, includes application of a first layer of coating onto the surface of the medical device, an imprint can be transferred to the coated surface and subsequently a second coating can be applied, or even a third layer. If desired or necessary, each additional coated surface can be imprinted with the pattern to improve adhesion qualities of the multiple layers to each other and to the medical device. The subsequent coating at least partially fills the area defined by the cavities. Further, the projections extend upwardly into the subsequent coating to provide greater surface area and greater adhesion qualities to the coating layers.

In one embodiment of the invention, the multiple layers of coatings can include different polymers, if desired. The polymer can be any polymer. For example, if desired, the polymer of the outermost layer can have a different dissolution rate than a polymer of an underlying layer.

In accordance with the invention, the coating can comprise any polymeric material. In this regard, the polymer can be hydrophilic, hydrophobic, biodegradable, or non-biodegradable. Further, in the event that the polymer includes a therapeutic agent, the polymer is any polymer in which the therapeutic agent, i. e., the drug, is substantially soluble. In this manner, one purpose of the polymer coating is to serve as a controlled release vehicle for the therapeutic agent or as a reservoir for a therapeutic agent to be delivered to the body, for example but not limitation, at the site of a lesion.

In accordance with the invention, material for the polymeric coating can be selected from the group consisting of polyacrylates, polymethacrylates, polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. Coatings prepared from polymeric dispersions including polyurethane dispersions (BAYHYDROL, etc.) and acrylic acid latex dispersions can also be used with the therapeutic agents of embodiments of the invention.

For the purpose of illustration and not limitation, biodegradable polymers that can be used in this invention include polymers including poly(L-lactic acid), poly(DL-lactic acid), polycaprolactone, poly(hydroxy butyrate), polyglycolide, poly(diaxanone), poly(hydroxy valerate), polyorthoester; copolymers including poly (lactide-co-glycolide), polyhydroxy (butyrate-co-valerate), polyglycolide-co-trimethylene carbonate; polyanhydrides; polyphosphoester; polyphosphoester-urethane; polyamino acids; polycyanoacrylates; biomolecules including fibrin, fibrinogen, cellulose, starch, collagen and hyaluronic acid; and mixtures of the foregoing. Biostable materials that are suitable for use in this invention include polymers including polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (including styrene acrylonitrile copolymers, ethylene methyl methacrylate copolymers, ethylene vinyl acetate), polyethers, rayons, cellulosics (including cellulose acetate, cellulose nitrate, cellulose propionate, etc.), parylene and derivatives thereat and mixtures and copolymers of the foregoing.

Other polymers that can be used in embodiments of this invention include, but are not limited to, those having the MPC subunit including poly(MPC$_w$:LAM$_x$:HPMA$_y$:TSMA$_z$) where w, x, y, and z represent the molar ratios of monomers used in the feed for preparing the polymer and MPC represents the unit 2-methacryoyloxyethylphosphorylcholine, LMA represents the unit lauryl methacrylate, HPMA represents the unit 2-hydroxypropyl methacrylate, and TSMA represents the unit 3-trimethoxysilylpropyl methacrylate.

Further, and as discussed above, the coating preferably includes a therapeutic agent. A wide variety of therapeutic agents can be included in the coating depending on the intended application of the medical device. For example and not limitation, the therapeutic agent can include be agents with anti-proliferative, anti-inflammatory, antineoplastic, antiplatelet, anti-coagulant, anti-fibrin, antithrombonic, antimitotic, antibiotic, antiallergic and antioxidant properties have been proposed for use with drug eluting stents (DESs). Examples of suitable therapeutic agents include synthetic inorganic and organic compounds, proteins and peptides, polysaccharides and other sugars, lipids, DNA and RNA nucleic acid sequences, antisense oligonucleotides, antibodies, receptor ligands, enzymes, adhesion peptides, blood clot agents such as streptokinase and tissue plasminogen activator, antigens, hormones, growth factors, ribozymes, retroviral vectors, anti-proliferative agents such as rapamycin (sirolimus), 40-O-(2-hydroxyethyl)rapamycin (everolimus), 40-O-(3-hydroxypropyl)raparnycin, 40-O-(2-hydroxyethyoxy) ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins such as sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä, calcium channel blockers such as nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements such as vitamins, anti-inflammatory agents such as aspirin, tacrolimus, dexamethasone and clobetasol, cytostatic substances such as angiopeptin, angiotensin converting enzyme inhibitors such as captopril, cilazapril or lisinopril, antiallergic agents is permirolast potassium, alpha-interferon, bioactive RGD, and genetically engineered epithelial cells. Other therapeutic agents which are currently available or that may be developed in the future for use with DESs may likewise be used and all are within the scope of this invention.

In one embodiment, the at least one therapeutic agent may be rapamycin. The therapeutic agent may be a therapeutic composition having zotarolimus and paclitaxel or derivatives, prodrugs, or salts thereof. The ratio of zotarolimus:paclitaxel, r, by weight may be $10:7 \leq r \leq 10:0.01$, for example.

In further accordance with the invention, the multiple layers of coatings can be include different therapeutic agents and/or therapeutic agents having different release rates. A therapeutic agent in the outermost layer will be released first, as the outermost layer dissolves and any therapeutic substance in an underlying layer will be released afterward.

It should be appreciated that the although the medical devices discussed herein are intended for the treatment of cardiovascular disease such as restenosis, the invention is not limited to medical devices for the treatment of cardiovascular diseases. In this regard, other treatable conditions include but are not limited to ischemic bowel diseases, inflammatory bowel diseases, necrotizing enterocolitis, intestinal inflammations/allergies including Coeliac diseases, proctitis, eosinophilic gastroenteritis, mastocytosis, Crohn's disease and ulcerative colitis; nervous diseases including multiple myositis, Guillain-Barre syndrome, Meniere's disease, polyneuritis, multiple neuritis, mononeuritis and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases including osteoporosis; respiratory diseases including sarcoidosis, fibroid lung and idiopathic interstitial pneumonia; skin disease including dermatomyositis, leukoderma vulgaris, ichthyosis vulgaris, photoallergic sensitivity and cutaneous T cell lymphoma; circulatory diseases including arteriosclerosis, atherosclerosis, aortitis syndrome, polyarteritis nodosa and myocardosis; collagen diseases including scleroderma, Wegener's granuloma and Sjogren's syndrome; adiposis; eosinophilic fasciitis; periodontal disease including lesions of gingiva, periodontium, alveolar bone and substantia ossea dentis; nephrotic syndrome including glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury including ischemia-reperfusion injury of organs (including heart, liver, kidney and digestive tract) which occurs upon preservation, transplantation or ischemic disease (for example, thrombosis and cardiac infarction); intestinal diseases including endotoxin-shock, pseudomembranous colitis and colitis caused by drug or radiation; renal diseases including ischemic acute renal insufficiency and chronic renal insufficiency; pulmonary diseases including toxinosis caused by lung-oxygen or drug (for example, paracort and bleomycins), lung cancer and pulmonary emphysema; ocular diseases including cataracts, siderosis, retinitis, pigmentosa, senile macular degeneration, vitreal scarring and corneal alkali burn; dermatitis including erythema multiforme, linear IgA ballous dermatitis and cement dermatitis; and others including gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-$C_4$ release; Behcet's disease including intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease including immunogenic diseases (for example, chronic autoimmune liver diseases including autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (including alcoholic cirrhosis) and hepatic failure including fulminant hepatic failure, late-onset hepatic failure and "acute-on-chronic" liver failure (acute liver failure on chronic liver diseases).

Therapeutic coatings can be used for implant devices that principally contact tissue, bone and/or blood. Examples of such devices include: heart valves, vascular grafts, sinus/neuro/urinary catheters, ventricular-assist devices, pumps, ligation clips, orthopedic pins, plates, replacement joints, bone prostheses, and the like.

It will be apparent to those skilled in the art that various modifications and variations can be made in the method and apparatus of the present invention without departing from the spirit or scope of the invention. Thus, it is intended that the present invention include modifications and variations that are within the scope of the appended claims and their equivalents.

What is claimed is:

1. A method of imprinting a pattern onto a surface of a medical device, the method comprising:
   providing a medical device having an outer surface;
   providing an imprinting apparatus comprising:
      a generally tubular body having a lumen therein configured to receive the medical device, and an inner surface including an imprint surface along a portion thereof, the imprint surface further including a plurality of projections extending outwardly from the imprint surface, a plurality of cavities extending inwardly from the imprint surface, or a combination thereof, each cavity having a depth and a width,
   positioning the medical device in the lumen of the imprinting apparatus;
   imprinting a pattern on the outer surface of the medical device by applying a compressive force on the imprinting apparatus; and
   applying a coating material to the patterned outer surface of the medical device.

2. The method of claim 1, wherein the medical device comprises a generally tubular structure.

3. The method of claim 2, wherein the method includes placing a mandrel in the lumen of the tubular structure and imprinting the pattern on an outer surface of the medical device.

4. The method of claim 1, wherein the medical device is a stent, graft, shaft or balloon.

5. The method of claim 1, wherein the patterned surface is at least a portion of the surface of the medical device.

6. The method of claim 1, wherein the layer of coating is applied to the surface of the medical device by at least one of spraying, jetting, or dipping techniques.

7. The method of claim 1, wherein the coating material includes at least one polymer.

8. The method of claim 7, wherein the at least one polymer is phosphorylcholine.

9. The method of claim 1, wherein the coating material includes at least one therapeutic agent.

10. The method of claim 9, wherein the at least one therapeutic agent is rapamycin.

11. The method of claim 1, wherein the applying step includes applying a second coating to at least a portion of the patterned surface of the medical device.

12. A method of imprinting a pattern onto a surface of a medical device, comprising:
    providing a medical device having a coated surface;
    imprinting a pattern on the coated surface of the medical device; and
    applying a coating material to the patterned surface of the medical device.

13. The method of claim 12, wherein the coated surface of the medical device includes at least one therapeutic agent.

14. The method of claim 12, wherein the coating material applied to the patterned surface of the medical device is configured to control the release of the at least one therapeutic agent.

15. A method of imprinting a pattern onto a surface of a medical device, comprising:
    providing a medical device having an outer surface, a generally tubular structure and a lumen defined therein;
    placing a mandrel in the lumen of the tubular structure;
    imprinting a pattern on the outer surface of the medical device; and
    applying a coating material to the patterned outer surface of the medical device.

16. The method of claim 15, wherein the medical device is a stent, graft, shaft or balloon.

17. The method of claim 15, wherein applying the coating material comprises at least one of spraying, jetting, or dipping techniques.

18. The method of claim 15, wherein the coating material includes at least one polymer.

19. The method of claim 18, wherein the at least one polymer is phosphorylcholine.

20. The method of claim 15, wherein the coating material includes at least one therapeutic agent.

21. The method of claim 20, wherein the at least one therapeutic agent is rapamycin.

22. The method of claim 15, wherein the imprinting step includes imprinting a pattern on a coated surface of the medical device.

23. The method of claim 11, wherein the coated surface of the medical device includes at least one therapeutic agent.

24. The method of claim 22, wherein the coating material applied to the patterned surface of the medical device is configured to control the release of the at least one therapeutic agent.

25. The method of claim 15, wherein the applying step includes applying a second coating to at least a portion of the patterned surface of the medical device.

* * * * *